(12) United States Patent
Nash (10) Patent No.: US 7,833,239 B2
(45) Date of Patent: *Nov. 16, 2010

(54) SYSTEM AND METHOD OF USE FOR REVASCULARIZING STENOTIC BYPASS GRAFTS AND OTHER BLOOD VESSELS

(75) Inventor: John E. Nash, Chester Springs, PA (US)

(73) Assignee: Kensey Nash Corporation, Exton, PA (US)

( * ) Notice: Subject to any disclaimer, the term of this patent is extended or adjusted under 35 U.S.C. 154(b) by 965 days.

This patent is subject to a terminal disclaimer.

(21) Appl. No.: 11/627,628

(22) Filed: Jan. 26, 2007

(65) Prior Publication Data

US 2007/0118072 A1    May 24, 2007

Related U.S. Application Data

(63) Continuation of application No. 10/665,337, filed on Sep. 18, 2003, now Pat. No. 7,534,249, which is a continuation of application No. 10/121,192, filed on Apr. 12, 2002, now Pat. No. 6,905,505, which is a continuation of application No. 09/594,131, filed on Jun. 14, 2000, now Pat. No. 6,524,323, which is a continuation of application No. 09/233,712, filed on Jan. 19, 1999, now Pat. No. 6,080,170, which is a continuation-in-part of application No. 08/900,598, filed on Jul. 25, 1997, now Pat. No. 5,879,361, which is a continuation-in-part of application No. 08/690,438, filed on Jul. 26, 1996, now Pat. No. 5,779,721.

(51) Int. Cl.
*A61B 17/22* (2006.01)

(52) U.S. Cl. .................................................. 606/159
(58) Field of Classification Search ................. 606/159, 606/167, 170, 180; 600/565, 566, 567, 568, 600/564, 22
See application file for complete search history.

(56) References Cited

U.S. PATENT DOCUMENTS 4,445,509 A    5/1984    Auth ........................... 128/305

(Continued)

FOREIGN PATENT DOCUMENTS

EP    0353087    1/1990

(Continued)

OTHER PUBLICATIONS

Kolodgie et al., "Local delivery of ceramide for restenosis: is there a future for lipid therapy?" Circulation Res., Aug. 18, 2000.

(Continued)

*Primary Examiner*—Kevin T Truong
(74) *Attorney, Agent, or Firm*—Woodcock Washburn, LLP (57) ABSTRACT

A system and method for opening a lumen in an occluded blood vessel, e.g., a coronary bypass graft, of a living being's vascular system. The system introduces an infusate liquid at a first flow rate to the occluded portion of the blood vessel, and withdraws that liquid and some blood at a second and higher flow rate. This action creates a differential flow in the occluded blood vessel portion and thereby prevent particles of occlusive material from flowing into any upstream blood vessel or downstream blood vessel in said living being's vascular system.

34 Claims, 3 Drawing Sheets

U.S. PATENT DOCUMENTS

| | | | |
|---|---|---|---|
| 4,589,412 A | 5/1986 | Kensey | 128/305 |
| 4,631,052 A | 12/1986 | Kensey | 604/22 |
| 4,679,558 A | 7/1987 | Kensey et al. | 128/328 |
| 4,686,982 A | 8/1987 | Nash | 128/305 |
| 4,696,667 A | 9/1987 | Masch | 604/22 |
| 4,700,705 A | 10/1987 | Kensey et al. | 128/341 |
| 4,747,821 A | 5/1988 | Kensey et al. | 604/22 |
| 4,749,376 A | 6/1988 | Kensey et al. | 604/22 |
| 4,762,129 A | 8/1988 | Bonzel | 606/194 |
| 4,775,371 A | 10/1988 | Mueller, Jr. | 606/192 |
| 4,790,813 A | 12/1988 | Kensey | 604/22 |
| 4,842,579 A | 6/1989 | Shiber | 604/22 |
| 4,857,045 A | 8/1989 | Rydell | 604/22 |
| 4,883,458 A | 11/1989 | Shiber | 604/22 |
| 4,898,575 A | 2/1990 | Fischell et al. | 604/22 |
| 4,957,482 A | 9/1990 | Shiber | 604/22 |
| 5,009,659 A | 4/1991 | Hamlin et al. | 606/159 |
| 5,022,553 A | 6/1991 | Pontius | 206/205 |
| 5,030,201 A | 7/1991 | Palestrant | 604/22 |
| 5,042,984 A | 8/1991 | Kensey et al. | 606/128 |
| 5,047,040 A | 9/1991 | Simpson et al. | 606/159 |
| 5,049,124 A | 9/1991 | Bales, Jr. | 604/22 |
| 5,074,841 A | 12/1991 | Ademovic | 604/22 |
| 5,087,265 A | 2/1992 | Summers | 606/159 |
| 5,097,849 A | 3/1992 | Kensey et al. | 128/898 |
| 5,114,399 A | 5/1992 | Kovalcheck | 604/22 |
| 5,120,308 A | 6/1992 | Hess | 604/170.01 |
| 5,135,483 A | 8/1992 | Wagner et al. | 604/22 |
| 5,195,956 A | 3/1993 | Stockmeier | 604/22 |
| 5,209,727 A | 5/1993 | Radisch, Jr. et al. | 604/96.01 |
| 5,224,945 A | 7/1993 | Pannek, Jr. | 606/159 |
| 5,267,955 A | 12/1993 | Hanson | 604/22 |
| 5,273,526 A | 12/1993 | Dance et al. | 604/35 |
| 5,282,484 A | 2/1994 | Reger | 128/898 |
| 5,284,486 A | 2/1994 | Kotula et al. | 606/159 |
| 5,314,407 A | 5/1994 | Auth et al. | 604/22 |
| 5,358,472 A | 10/1994 | Vance et al. | 604/22 |
| 5,366,463 A | 11/1994 | Ryan | 606/159 |
| 5,368,603 A | 11/1994 | Haliburton | 606/159 |
| 5,370,609 A | 12/1994 | Drasler et al. | 604/22 |
| 5,370,651 A | 12/1994 | Summers | 606/159 |
| 5,385,152 A | 1/1995 | Abele et al. | 600/585 |
| 5,395,311 A | 3/1995 | Andrews | 604/22 |
| 5,402,790 A | 4/1995 | Jang et al. | 600/471 |
| 5,409,454 A | 4/1995 | Fischell et al. | 604/22 |
| 5,423,742 A | 6/1995 | Theron | 604/28 |
| 5,429,136 A | 7/1995 | Milo et al. | 600/439 |
| 5,462,529 A | 10/1995 | Simpson et al. | 604/101.04 |
| 5,496,267 A | 3/1996 | Drasler et al. | 604/22 |
| 5,632,755 A | 5/1997 | Nordgren et al. | 606/159 |
| 5,665,098 A | 9/1997 | Kelly et al. | 606/159 |
| 5,665,103 A | 9/1997 | Lafontaine et al. | 606/192 |
| 5,679,558 A | 10/1997 | Gobel et al. | 800/292 |
| 5,681,336 A | 10/1997 | Clement et al. | 606/159 |
| 5,779,721 A | 7/1998 | Nash | 606/159 |
| 5,833,650 A | 11/1998 | Imran | |
| 5,836,892 A | 11/1998 | Lorenzo | 600/585 |
| 5,868,767 A | 2/1999 | Farley et al. | 606/159 |
| 5,879,361 A | 3/1999 | Nash | 606/159 |
| 5,882,329 A | 3/1999 | Patterson et al. | 604/500 |
| 5,900,246 A | 5/1999 | Lambert | 424/429 |
| 5,947,985 A | 9/1999 | Imran | 606/159 |
| 5,954,745 A | 9/1999 | Gertler et al. | 606/200 |
| 5,976,153 A | 11/1999 | Fischell et al. | 623/1.11 |
| 6,017,319 A | 1/2000 | Jacobsen et al. | 600/585 |
| 6,074,407 A | 6/2000 | Levine et al. | 606/194 |
| 6,080,170 A | 6/2000 | Nash et al. | 606/159 |
| 6,093,157 A | 7/2000 | Chandrasekaran | 600/585 |
| 6,126,667 A | 10/2000 | Barry et al. | 606/159 |
| 6,135,991 A | 10/2000 | Muni et al. | 604/509 |
| 6,217,567 B1 | 4/2001 | Zadno-Azizi et al. | 604/530 |
| 6,235,042 B1 | 5/2001 | Katzman | 606/159 |
| 6,264,672 B1 | 7/2001 | Fisher | 606/200 |
| 6,296,616 B1 | 10/2001 | McMahon | 600/585 |
| 6,319,244 B2 | 11/2001 | Suresh et al. | 604/525 |
| 6,344,049 B1 | 2/2002 | Levinson et al. | 606/200 |
| 6,436,056 B1 | 8/2002 | Wang et al. | 600/585 |
| 6,482,217 B1 | 11/2002 | Pintor et al. | 606/159 |
| 6,524,323 B1 | 2/2003 | Nash et al. | 606/159 |
| 6,544,276 B1 | 4/2003 | Azizi | |
| 6,652,480 B1 | 11/2003 | Imran et al. | 604/35 |
| 6,905,505 B2 | 6/2005 | Nash et al. | 606/159 |
| 7,235,088 B2 * | 6/2007 | Pintor et al. | 606/159 |
| 7,479,147 B2 * | 1/2009 | Honeycutt et al. | 606/159 |
| 2004/0097995 A1 | 5/2004 | Nash et al. | 606/159 |

FOREIGN PATENT DOCUMENTS

| | | |
|---|---|---|
| EP | 0806212 | 11/1997 |
| WO | 92/21386 | 12/1992 |
| WO | 93/00119 | 1/1993 |
| WO | 95/21576 | 8/1995 |
| WO | 98/04199 | 2/1998 |
| WO | 99/21510 | 5/1999 |
| WO | 00/54659 | 9/2000 |
| WO | 00/67647 | 11/2000 |
| WO | 01/10313 | 2/2001 |

OTHER PUBLICATIONS

Charles et al., "Ceramide-coated balloon catheters limit neointimal hyperplasia after stretch injury in carotid arteries," Circulation Res., Aug. 18, 2000, 87:287.

Bonan, "Local drug delivery for the treatment of thrombus and restenosis," J. of Invasive Cardiology, Oct. 1996, 8:399-408.

Rotoblator; Heart Technology, Inc.

Extraction Atherectomy, Putting Plaque and Thrombus in their Proper Place; Interventional Technologies, Inc.

AngioJet Rapid Thrombectomy System; Possis Medical Inc. Innovations for Life; May 1996.

Rheolytic Thrombectomy System AngioJet; Possis Medical, Inc. Innovations for Life.

Amplatz Thrombectomy Device, The Clot-Buster; Microvena Corporation.

* cited by examiner

SYSTEM AND METHOD OF USE FOR REVASCULARIZING STENOTIC BYPASS GRAFTS AND OTHER BLOOD VESSELS

CROSS REFERENCE TO RELATED APPLICATIONS

This application is a continuation of application Ser. No. 10/665,337 filed Sep. 18, 2003, entitled System and method of Use for Agent Delivery and Revascularizing of Grafts and Vessels, now pending, which is a continuation of application Ser. No. 10/121,192, filed Apr. 12, 2002, now U.S. Pat. No. 6,905,505, which is a continuation of application Ser. No. 09/594,131, filed on Jun. 14, 2000, now U.S. Pat. No. 6,524,323, which is a continuation of U.S. patent application Ser. No. 09/233,712, filed on Jan. 19, 1999, now U.S. Pat. No. 6,080,170, which is a continuation-in-Part of U.S. patent application Ser. No. 08/900,598, filed on Jul. 25, 1997, now U.S. Pat. No. 5,879,361, which in turn is a continuation-in-part of U.S. application Ser. No. 08/690,438, filed on Jul. 26, 1996, now U.S. Pat. No. 5,779,721, all of which are assigned to the same assignee as this invention, and whose disclosures are incorporated by reference herein.

FIELD OF THE INVENTION

This application relates generally to medical instruments and methods of use to remove occlusive material from a vessel, duct or lumen within the body of a living being.

BACKGROUND OF THE INVENTION

Catheter instruments have been suggested or disclosed in the patent literature for effecting non-invasive or minimally invasive revascularization of occluded arteries. For example, in U.S. Pat. No. 4,445,509 there is disclosed a recanalization catheter designed specifically for cutting away hard, abnormal deposits, such as atherosclerotic plaque, from the inside of an artery, while supposedly preserving the soft arterial tissue. That recanalizing catheter includes a sharp-edged, multi-fluted, rotating cutting tip mounted at the distal end of the catheter and arranged to be rotated by a flexible drive shaft extending down the center of the catheter. The rotation of the cutting head is stated as producing a "differential cutting" effect, whereupon relatively hard deposits are cut away from relatively soft tissue. Suction ports are provided to pull the hard particles produced by the cutting action into the catheter for removal at the proximal end thereof so that such particles do not flow distally of the catheter where they could have an adverse effect on the patients' body.

In U.S. Pat. No. 4,700,705, which is assigned to the same assignee as this invention and whose disclosure is incorporated by reference herein, there are disclosed and claimed catheters and methods of use for effecting the opening of a vessel, duct or lumen, such as the opening of an atherosclerotic restriction (partial or total occlusion) in an artery. These catheters are elongated flexible members of sufficient flexibility to enable them to be readily passed through the body of the patient to the situs of the atherosclerotic plaque in the artery to be opened. A working head is mounted at the distal end of the catheter and is arranged for high-speed rotation about the longitudinal axis of the catheter. In some embodiments the catheter may eject fluid at the working head to expedite the restriction-opening procedure.

In U.S. Pat. No. 4,747,821, which is also assigned to the same assignee as this invention and whose disclosure is incorporated by reference herein, there is disclosed and claimed other catheters particularly suited for revascularization of arteries. Each of those catheters includes a rotary working head having at least one non-sharp impacting surface to effect material removal without cutting. Moreover, those catheters are arranged to eject fluid adjacent the working head to expedite the revascularization procedure. In particular, the rotation of the working head produces a powerful, toroidal shaped vortex contiguous with the working head which has the effect of recirculating any particles that may have been broken off from the material forming the arterial restriction so that the working head repeatedly impacts those particles to reduce their size.

In U.S. Pat. No. 5,042,984, which is also assigned to the same assignee as this invention and whose disclosure is incorporated by reference herein, there are disclosed and claimed catheters whose working heads include impacting surfaces of differing aggressiveness which may be selectively brought into engagement with the restriction to be opened. Such catheters also make use of exiting jets of liquid as described above.

Other atherectomy devices for enlarging an opening in a blood vessel have been disclosed and claimed in the following U.S. Pat. No. 4,589,412 (which is assigned to the same assignee as this invention and whose disclosure is incorporated by reference herein); U.S. Pat. No. 4,631,052; U.S. Pat. No. 4,686,982 (which is assigned to the same assignee as this invention and whose disclosure is incorporated by reference herein); U.S. Pat. No. 4,749,376 (which is assigned to the same assignee as this invention and whose disclosure is incorporated by reference herein); U.S. Pat. Nos. 4,790,813; 5,009,659; 5,074,841; 5,282,484; 5,366,463; 5,368,603; 5,402,790; 5,423,742; and U.S. Pat. No. 5,429,136.

Some rotary atherectomy devices are in use in this country for revascularizing occluded arteries. However, their use is limited to some very selected applications. Thus, in many instances a vascular occlusion of a coronary artery can only be treated by coronary bypass surgery wherein a graft, e.g., a saphenous vein section and/or mammary artery section, is surgically shunted across the occluded coronary artery. Unfortunately a significant percentage of bypass surgical grafts become re-occluded over time. Thus, the re-occluded graft has to be either bypassed by another graft (i.e., second bypass surgery), or the re-occluded graft has to be revascularized (i.e., its lumen reopened) by some intravascular procedure. If the occluded graft is not totally occluded, balloon angioplasty may be indicated to reopen the graft. Where, however, the graft is totally occluded balloon angioplasty in unavailable. Thus, if revascularization of that graft is desired, resort may be to rotary atherectomy.

One currently available rotary atherectomy device is the ROTOBLACOR® System of Heart Technology, Inc. That system utilizes a catheter having a diamond coated elliptical burr which is rotated at a high rate of speed, e.g., up to 190,000 rpm. The burr serves to break the atherosclerotic plaque into fine particles which are allowed to remain in the patient's body for disposal by the patient's reticuloendothelial system.

As is known to those skilled in the art, one problem with a rotary atherectomy device is that unless the debris produced is so small and benign that it can be left within the patient's vascular system there must be some means to ensure that the debris does not flow upstream into the aorta during the procedure or into the downstream artery graft at the breakthrough point when the device comes out the distal side of a total occlusion, since either action could present a significant hazard to the patient. In particular, the former route risks stroke, and the later route risks local ischemia of heart muscle when debris blocks off small arteries.

Thus, the collection and/or aspiration of debris produced during the revascularization of occluded arterial bypass grafts or other blood vessels is getting considerable attention in the medical arts. For example, Possis Medical, Inc., the assignee of U.S. Pat. Nos. 5,370,609 and 5,496,267, provides catheter devices designated as the ANGIOJET Rapid Thrombolectomy System and the ANGIOJET Rheolytic Thrombolectomy System. These devices are presumably constructed in accordance with those patents and are believed to be presently undergoing clinical trials. The catheter devices disclosed in those patents utilize high velocity jets of saline to abrade the blockage. In particular, the patents disclose utilizing the momentum of the saline jets to create a local vacuum to entrain any particulate material produced by the revascularization procedure, with the momentum and the local positive pressure being sufficient to carry the saline and debris to a return collection bag.

Another atherectomy device which is currently undergoing clinical trials is the Coronary TEC® System of Interventional Technologies, Inc. That device is believed to be the subject of U.S. Pat. No. 5,224,945, and basically comprises a catheter having a working head with microtome sharp blades for cutting plaque circumferentially. The excised plaque is extracted by suction through a central lumen in the catheter into an exteriorly-located vacuum bottle. No control of the quantity of flow of the debris-carrying fluid from the catheter is disclosed.

U.S. Pat. No. 5,030,201 (Palestran) discloses a system including an expandable atherectomy catheter arranged to be rotated to cut through an occluded artery to revascularize it. The atherectomy catheter includes an expandable cutting head having plural elongated cutting members which are mounted on a flexible torque tube incorporating a vacuum or aspiration system for retrieval of excised material. The cutting head is arranged to be rotated to cause the elongated members to cut away atheromatous material or blood clots. The atherectomy catheter is arranged to be inserted into the blood vessel through a coaxial delivery catheter, also forming a part of the system. The mechanism for aspirating particles of atheromatous material or blood clots removed by the elongated cutting members is disclosed as being in the form of a vacuum port provided at the proximal end of either the delivery catheter, the atherectomy catheter or a "retracting catheter" which also constitutes a part of the system. Saline solution or some other irrigant is infused through one of the catheters of the device that is not being used for aspiration. The infusion rate of the saline solution is balanced with the aspiration rate to avoid any net removal of fluid from the vessel. In particular, the patent teaches that by balancing the infusion rate of the saline solution to the aspiration rate, the net removal of fluid from the vessel can be brought close to zero, thereby minimizing blood loss.

While the balancing of the infusion and aspiration flow rates to minimize blood loss may be desirable, such action does not insure positive removal of all debris produced during the revascularization procedure.

Accordingly, a need exists for apparatus and a method of use to revascularize partially or totally occluded blood vessels, while positively assuring that any particles produced during the revascularization procedure are removed from the patient's body. In the case of partially or totally occluded coronary bypass grafts, a need exists for intravascular atherectomy apparatus and methods of use for effectively producing a lumen through the occlusion for the free flow of blood, without the risk that any debris produced during the lumen opening procedure will enter into the aorta or downstream of the occlusion once it has been crossed or opened.

OBJECTS OF THE INVENTION

Accordingly, it is a general object of this invention to provide systems and methods which address those needs.

It is another object of this invention to provide a system and methods for effectively revascularizing partially or totally occluded blood vessels and for removing any debris produced during the procedure from the patient's body.

It is another object of this invention to provide a system and methods for safely revascularizing partially or totally occluded blood vessels.

It is still another object of this invention to provide a system and methods for effectively opening a lumen in a partially or totally occluded arterial bypass graft, without the risk of debris produced during the procedure entering the aorta or from flowing downstream once the lumen through the occlusion has been opened.

It is yet another object of this invention to provide a system and methods for effectively opening a lumen in a partially or totally occluded portion of an artery, e.g., the femoral artery, downstream of a junction with another vessel, e.g., the profunda femoris, without the risk of debris produced during the procedure entering the other vessel or from flowing downstream in the artery once the lumen through the occlusion has been opened.

It is yet a further object of this invention to provide a system and methods for revascularizing partially or totally occluded blood vessels utilizing liquid infusion and aspiration means for establishing a differential flow to positively ensure the aspiration of debris produced during the revascularization procedure.

It is yet a further object of this invention to provide a system and methods for revascularizing partially or totally occluded blood vessels utilizing liquid infusion and aspiration means which is easy to operate to effect the positive removal of debris produced during the revascularization procedure.

It is yet a further object of this invention to provide a system and methods for revascularizing partially or totally occluded blood vessels utilizing liquid infusion and aspiration means which is adjustable for effectuating the positive removal of debris produced during the revascularization procedure.

SUMMARY OF THE INVENTION

These and other objects of this invention are achieved by providing a system for opening a lumen in an occluded blood vessel, e.g., a coronary bypass graft, of a living being's vascular system located downstream of another blood vessel, e.g., the aorta, from which blood will flow to the occluded blood vessel. The system basically comprises a working head for revascularizing the vessel and means for extracting or removing debris produced by operation of the working head.

The working head, e.g., a rotary impacting impeller, is arranged to operate on, e.g., engage, material, such as an atherosclerotic deposit or lesion or thrombus forming the occlusion within the interior of the occluded blood vessel to open a lumen for the flow of blood therethrough.

The debris extraction means is arranged to introduce an infusate liquid at a first flow rate into the vessel adjacent the working head and to withdraw that liquid and some blood at a second and higher flow rate from the vessel. This action creates a differential flow in the vessel, whereupon debris within the vessel which is produced by the action of the working head on the occlusion material is positively withdrawn with the infusate liquid and blood from the vessel for remote collection, e.g., in a collection vessel located outside the body of the person being treated. Thus, the differential flow serves to prevent the debris from flowing into adjacent blood vessels, e.g., the aorta.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein.

DETAILED DESCRIPTION OF ILLUSTRATIVE EMBODIMENTS

Figure 1:
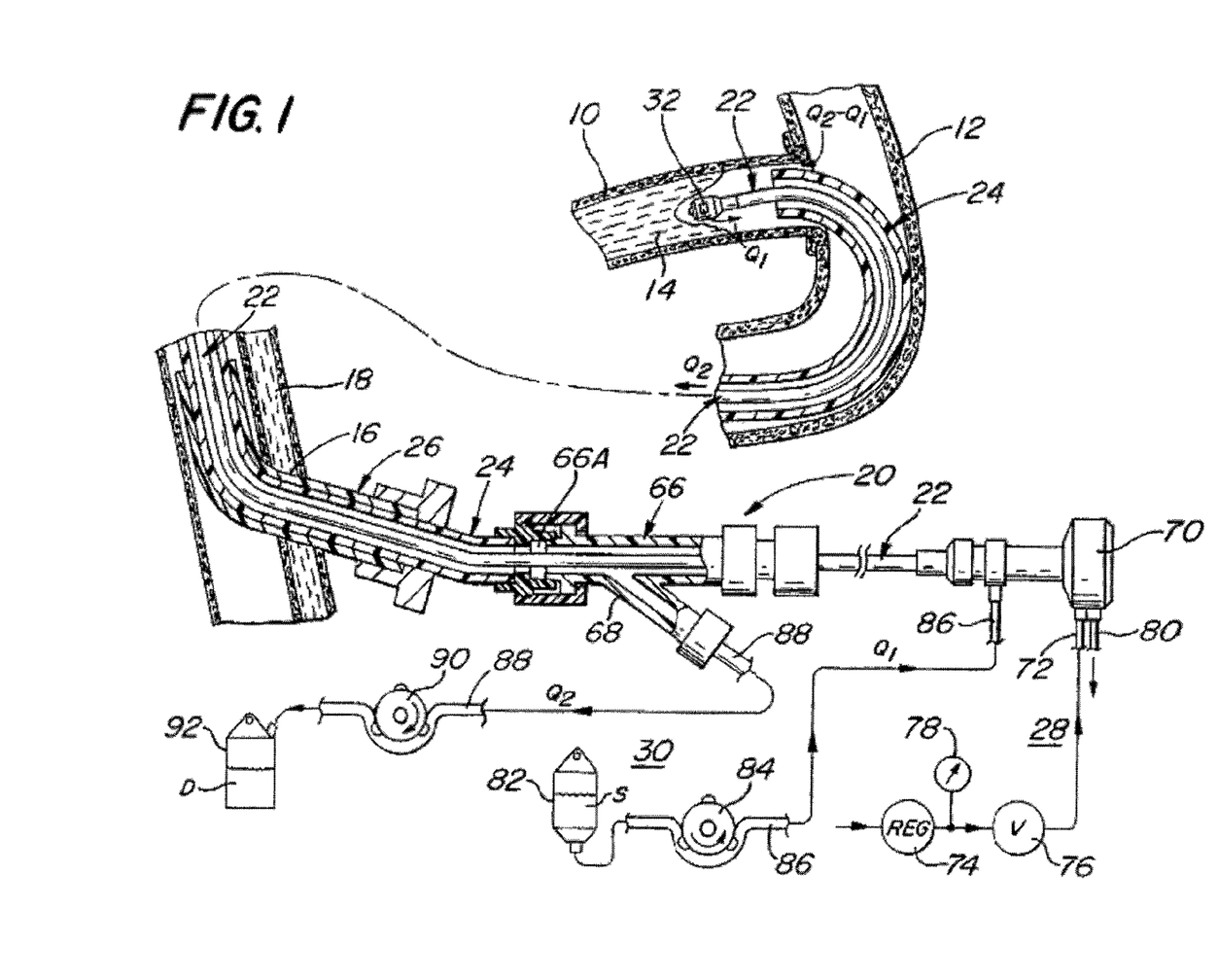
FIG. 1 is a schematic diagram, partially in section, of a system of the subject invention shown during the process of opening a lumen in a totally occluded coronary bypass graft so that blood can flow therethrough.
Figure 2:
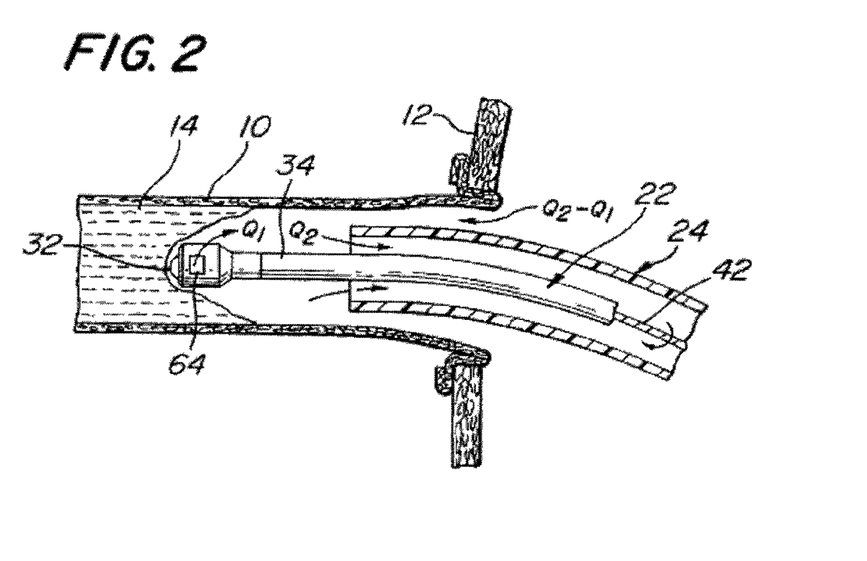
FIG. 2 is an enlarged view, partially in section, of a portion of the system of FIG. 1 shown during the process of opening a lumen in the occluded coronary bypass graft.

Referring now in greater detail to the various figures of the drawings wherein like reference characters refer to like parts, there is shown at 20 in FIG. 1 a system for revascularizing or opening a lumen through a coronary bypass graft which has become occluded, such as by the formation of a stenotic lesion or the build-up of plaque therein. As used herein the term "occluded" is given its broadest interpretation. Thus, an "occluded" graft or blood vessel may be either totally blocked or only partially blocked (i.e., there is a passageway or lumen through which some blood may flow).

The system 20 is arranged to be used for forming or enlarging a lumen through any blood vessel within the body of a living being, e.g., an occluded femoral artery downstream of the profunda femoris, not necessarily an occluded coronary bypass graft or an occluded coronary artery. In particular, the system 20 is arranged to produce a channel or lumen or to enlarge a lumen through the occlusive material with the vessel and to ensure that any particles of that material which are removed or broken away, during the revascularization procedure are prevented from flowing into the contiguous vascular system. When the system 20 is used for revascularization of occluded coronary bypass grafts, a primary application for the system 20, the debris produced is drawn into the system for extracorporeal removal and is thus prevented from entering the aorta.

As can be seen in FIG. 1, the system 20 basically comprises an "atherectomy" catheter 22, a guide catheter 24, an introducer sheath 26, a drive sub-system 28, and a debris removal sub-system 30. The atherectomy catheter 22 is in the form of an elongated flexible tubular body member or jacket at the free or distal end of which is located a rotatable working head 32. The working head 32 is generally similar to that described in U.S. Pat. No. 4,747,821. Alternatively, the working head may be constructed in accordance with the teachings of U.S. Pat. Nos. 4,679,558, 4,686,982, 4,749,376, 5,042,984, and 5,097,849, all of which are also assigned to the same assignee as this invention, and whose disclosures are also incorporated by reference herein. In fact, the working head may be any device for opening a lumen through the occlusive material.

In use the atherectomy catheter 22 is guided through the vascular system of the patient by the guide catheter 24 (which is conventionally placed) to the site of the vascular occlusion that has been determined to exist, so that the rotary working head is located immediately adjacent the upstream end of the occlusion. In the embodiment shown in FIG. 1, the atherectomy catheter is located within a coronary bypass graft 10 having an upstream end in fluid communication with the aorta 12. The downstream end of the graft is not shown and is in fluid communication with the coronary artery being bypassed or with smaller arteries of the heart. In the example shown herein the graft 10 is totally occluded by an atherosclerotic lesion or plaque or some other occlusive material 14 within the interior of the graft.

The atherectomy catheter 22 is introduced into the patient's vascular system in a conventional manner, e.g., via the use of the introducer sheath and guide catheter. As shown, this is accomplished via a percutaneous puncture 16 in the femoral artery 18. The sheath 26 and guide catheter 24 are each of conventional construction and thus their details will not be described in the interest of brevity.

The working head 32 is arranged to rotate about the longitudinal axis of the catheter at a high rate of speed, e.g., from 10,000 rpm to 200,000 rpm to repeatedly mechanically impact the occlusive material. At the same time, an infusate liquid (to be described later) is pumped through the atherectomy catheter by a pump (to be described later and forming a portion of the debris removal sub-system 30) and out of distal end of the atherectomy catheter adjacent the working head.

The opening of the occlusion to allow freer flow of blood therethrough is effected by impacting surfaces of the rotating working head impacting the occlusive material 14, whereupon portions thereof are removed, e.g., broken away. In addition, as will be described later, the rotation of the working head produces a powerful, toroidal shaped vortex contiguous with the working head. This vortex flow has the effect of recirculating any particles that are broken off from the occlusive material by the impact of the rotary working head's impacting surfaces back into contact with such surfaces. Accordingly, those particles are repeatedly impacted over and over, with each impaction reducing the size of the particles further until the resulting particle size is very small, e.g., 95% have a surface area less than that of a red-blood cell. At the same time another pump (also to be described later) of the debris removal sub-system 30 is operated to aspirate the particles produced during the revascularization procedure along with the infusate liquid and some blood.

Thus, as will be described in detail later, the debris removal subsystem 30 is operative to ensure that debris produced as the working head opens a lumen through the occlusion is not able to flow upstream into the upstream vessel, e.g., the aorta 12, during the lumen opening procedure, and once the working head breaks through or exits the occlusion on the downstream side, that the debris is not able to flow downstream into the downstream blood vessel(s).

Figure 4:
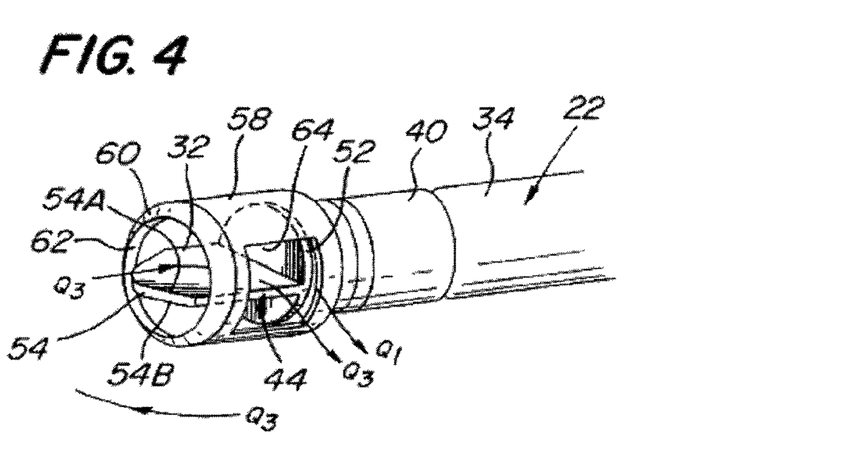
FIG. 4 is a reduced isometric view of the portion of the system shown in FIG. 3.

As best seen in FIG. 4 the atherectomy catheter includes a jacket 34 which is formed of any suitable material, e.g., plastic, and has a small outside diameter. In the preferred embodiment shown herein, the outside diameter of the jacket 34 is approximately 1.5 mm (5 French). This size catheter is merely exemplary. The means for effecting the rotation of the working head is the heretofore identified drive sub-system 28. That subsystem is similar to the drives disclosed in the aforementioned U.S. Pat. Nos. 4,686,982, and 4,747,821 and basically comprises an air-turbine motor and associated rotary drive cable (to be described later). Other drive systems can be utilized, as well.

Irrespective of the construction of the drive system, it is coupled to the working head 32 so that the working head is rotated about its longitudinal axis at the high rate of speed. Many of the details of the working head will be described later. Suffice it for now to say that the working head 32 includes an impeller portion 44 and a central shank portion or axle 36 (FIG. 4) projecting proximally therefrom. The axle 36 is supported in a central bore of a bushing 38 fixedly mounted at the distal end of the catheter's jacket 34 by an encircling mounting band 40. The shank 36 is fixedly secured to the distal end of a flexible drive cable 42 forming a portion of the drive sub-system 28.

The impeller 44 forms the distal portion of the working head and is fixedly secured to the shank 36 so that it will be rotated at a high rate of speed about its longitudinal axis by the concomitant rotation of the drive cable. The impeller portion 44 comprises a circular disk or base 52 from which a generally planar tip 54 projects. The tip 54 has a pair of generally planar diametrically disposed relieved side surfaces or faces which merge with an arcuate front or distal surface to form a pair of arcuate impacting surfaces 54A and 54B. Each of the impacting surfaces is radiused in a plane perpendicular to the axis of rotation of the working head so that each is not sharp, e.g., is in the range of approximately 0.001 inch to approximately 0.008 inch, although in the scale of the figures of the drawing they appear to be a sharp line.

The working head is located within a cylindrical shroud 56 (FIGS. 3 and 4) fixedly mounted on the front of the bushing 38. The shroud 56 includes a cylindrical sidewall portion 58 and a generally conical distal wall portion 60 terminating in a circular opening 62 in the distal end thereof. The shroud may be of any suitable outside diameter, e.g., 7 to 8 French. The distal arcuate portion of the impeller tip 54 projects out of the central or front opening 62. A side port or open window 64 is located in the sidewall 58.

As mentioned earlier the system 20 utilizes an infusate liquid to expedite the revascularization of the vessel. In particular, the infusate liquid is pumped at a flow rate $Q_1$ (to be described later) down through the interior of the catheter jacket 34 through four equidistantly spaced grooves 46 extending down the central bore of the bushing 38 and via radial ports 48 to an annular recess 50 in the front wall of the bushing. The annular recess is in fluid communication with the side port or window 64 in the shroud so that the infusate liquid can exit therefrom. The direction of flow of the infusate liquid down the atherectomy catheter and out the shroud at its working head is shown clearly in FIG. 4.

Figure 3:
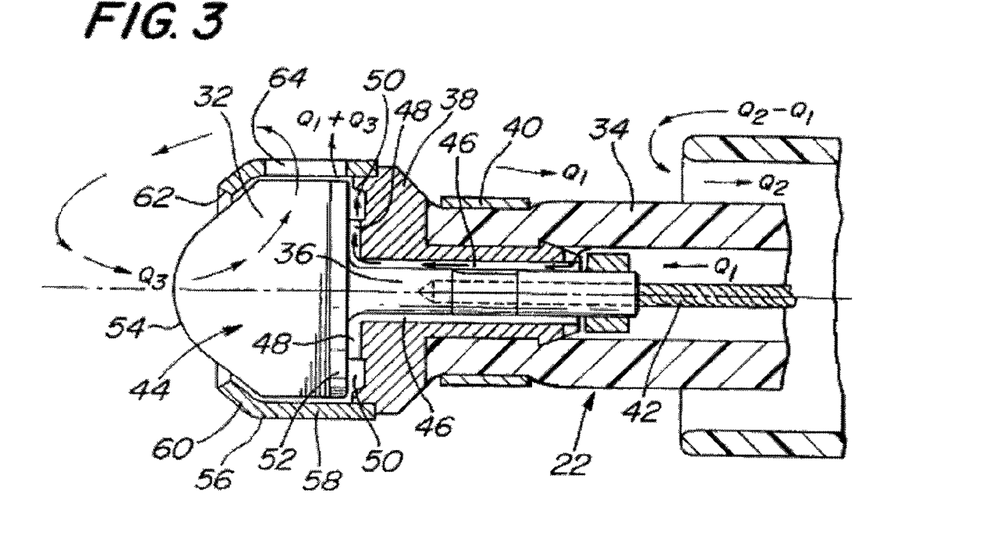
FIG. 3 is an even more greatly enlarged view, partially in section, of a portion of the system shown in FIG. 2.

The rotation of the working head about its longitudinal axis produces a powerful toroidal shaped vortex flow $Q_3$ in the fluid contiguous with the working head. This flow $Q_3$ circulates by entering into the shroud through the central or front opening 62 and exits out through the side window 64 as shown in FIG. 3. Thus, the flow exiting through window 64 is $Q_1+Q_3$. As will be appreciated by those skilled in the art the vortex flow $Q_3$ has the effect of recirculating any particles that are broken off from the occlusive material 14 by the action of the rotating working head back into contact with the working head's impacting surfaces. Thus, the occlusive material particles which are broken away are progressively reduced in size until they are aspirated by aspiration means forming a portion of the debris removal sub-system 30. That means will be described later. Suffice it for now to state that the aspiration means withdraws the infusate liquid, the debris particles and some blood at an aspiration flow rate of $Q_2$.

As should be appreciated by those skilled in the art the liquid exiting from the window 64 of the shroud will tend to push the atherectomy catheter's distal end sideways or laterally in the direction opposite to the direction of the liquid exiting that window. This hydrodynamic action can be effectively used to steer the catheter to a desired position with respect to an occlusion to be revascularized. In this regard, for example, when negotiating a branch in the artery system to reach the occlusion to be revascularized, the atherectomy catheter can be rotated or twisted about its longitudinal axis so that the shroud's window is facing in the opposite direction to the branch to be entered. This action will cause the side directed liquid exiting the window 64 to push the catheter's distal end sideways, whereupon it can enter the desired arterial branch. Such "hydrodynamic steering" of the atherectomy catheter can be accomplished in other manners and by other means than by the use of a shroud having a single side window or port. Thus, this invention contemplates an intravascular catheter instrument, of any type, including any means for producing an asymmetric, e.g., side directed, fluid flow adjacent the distal end of the catheter so that it can be steered into a desired position by appropriate rotation of the catheter about its longitudinal axis.

As mentioned earlier, the guide catheter 24 is of any conventional construction. In the preferred embodiment shown in FIG. 1 it is a 10F to 12F catheter having a conventional Y connector 66 at its proximal end. The Y connector 66 has one input leg including a Touhy-Borst adjustable hemostasis valve 66A through which the atherectomy catheter 22 passes. The other input leg, i.e., the angled leg 68, is connected to the aspiration portion of the debris removal sub-system 30 (to be described later).

Power for operating the atherectomy catheter is provided by the drive sub-system 28. That system includes an air turbine motor 70 which is coupled to the proximal end of the flexible drive cable 42. The air turbine 70 is provided with compressed air via an input line or conduit 72. Air for the line 72 is provided from a source (not shown) via an associated regulator 74, and the conventional control valve 76. The control valve is coupled to the input line 72 of the air turbine. A pressure gauge 78 is connected between the regulator 74 and the control valve 76. The regulator 74, the control valve 76, the pressure gauge 78 and the associated lines or conduits and the air source make up the drive sub-system 28. The control valve 76 is of any conventional construction, be it mechanical or electrical. The air turbine motor 70 is also of any conventional construction, as is the regulator 74 and the pressure gauge 78. The air turbine includes an outlet port in communication with the ambient atmosphere, via a line 80. It must be pointed out at this juncture that the atherectomy catheter 22 need not utilize an air turbine motor to rotate the working head. For example, an electric motor can be provided to replace the air turbine to drive the rotating cable and the associated working head. The debris removal sub-system 30 basically comprises a source 82 of the infusate liquid "S", e.g., saline plus a 30% contrast media, a first positive displacement pump 84, an input line or conduit 86, an outlet line or conduit 88, a second positive displacement pump 90, and a debris collection vessel 92. The input line 86 and its associated components, i.e., the pump 84 and infusate source 82 serve as the "infusion" means for the system 20. To that end the input line 86 is coupled via a connector to the interior of the atherectomy catheter, i.e., to the annular space within the catheter's jacket between it and the drive cable. The infusate liquid S is pumped at the flow rate $Q_1$ by the positive displacement pump 84 through line 86 from the supply or source 82. Thus, the infusate liquid S exits the catheter's working head and circulates as described earlier.

The rate of flow $Q_1$ of the infusate liquid is established by the positive displacement pump 84 under control of some automatic or manual controller (not shown). In accordance with one exemplary method of use the pump is operated to produce a flow rate $Q_1$ the range of 5-80 ml. per minute.

The output line 88 and its associated components, i.e., the pump 90 and debris collector vessel 92 serve as the "aspirating" means for the debris removal sub-system 30. To that end, the aspiration line 88 is connected to the leg 68 of the Y connector 66. The pump 90 is arranged to be operated to pump the infusate liquid, the debris produced by the revascularization, and some small amount of blood at the flow rate $Q_2$ in the proximal direction through the annular space between the atherectomy catheter 22 and the guide catheter 24 and out through the connector leg 68 into the outlet line 88, and from there to the collector vessel 92.

The flow rate $Q_2$ is selected to be greater than $Q_1$. For example, in one exemplary method of use the flow rate is selected to be in the range of 5-100 ml. per minute, with the differential between $Q_2$ and $Q_1$ being between 5 and 50 percent. The use of an aspiration flow rate $Q_2$ which is higher than the infusion flow rate $Q_1$ insures that any debris, e.g., particles of the occlusive material making up the graft's lesion, produced from debriding that material is positively prevented from flowing into adjacent vessel portions. In this regard, as will be appreciated by those skilled in the art, since the aspiration flow rate $Q_2$ is greater than the infusion flow rate $Q_1$, some blood equal to $Q_2-Q_1$ will also be withdrawn from the upstream vessel, e.g., the aorta as shown in FIGS. 1 and 3. The withdrawal of some blood from that vessel insures that the debris produced cannot flow upstream to enter into it. Instead the debris particles will be entrained within the infusate liquid and blood which is withdrawn through the aspiration line. The rate of blood withdrawn is preferably be kept to a minimum, e.g., 40 ml. per minute in the interests of patient safety.

In accordance with a preferred aspect of this invention the operation of the pumps 84 and 90 are coordinated so that $Q_2$ is equal to some variable times $Q_1$, where that variable is greater than 1 and is adjustable to accommodate the needs of the patient. Moreover, the coordination of the flow rates is preferably accomplished. automatically, so that a change in one flow rate automatically results in a proportional change in the other flow rate. This coordinated action may be accomplished by a mechanical linkage between the pumps, or by a common electrical controller for the pumps. Manual control of the pumps is also envisioned for some applications.

In any case, any suitable positive displacement pumps can be utilized, e.g., peristaltic pumps or piston pumps, in the system.

In order to expedite the revascularization of the bypass graft, the infusate liquid may be provided with a contrast medium, e.g., 30% contrast medium, so that the revascularization procedure can be viewed using conventional imaging techniques. Moreover, the infusate liquid can, if desired, be oxygenated to eliminate distal ischemia when the catheter is used for arterial restriction opening procedures. Also, if desired, small amounts of heparin, urokinase, etc., or other drugs can be added to the infusate liquid for the procedure.

Figure 5:
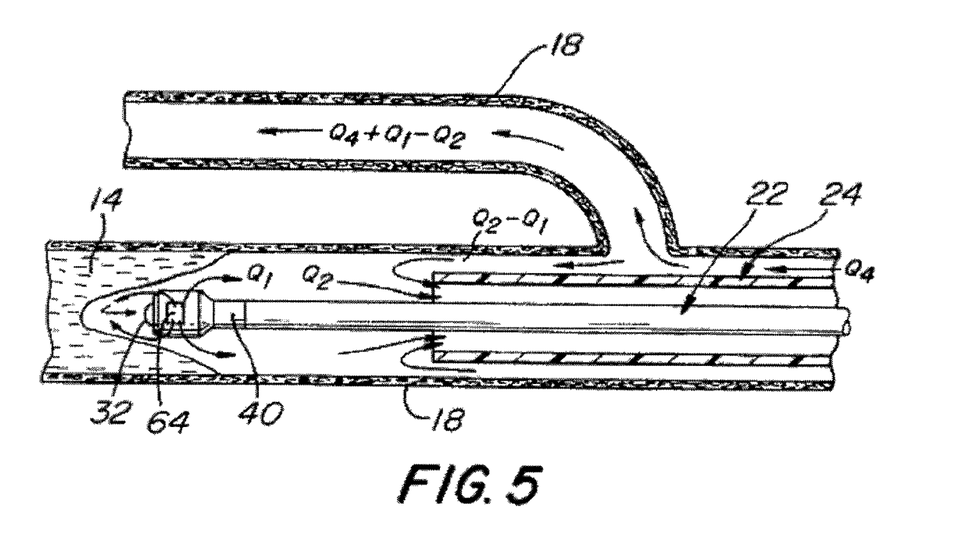
FIG. 5, is an illustration showing the apparatus of FIG. 1, partially in section, during the process of revascularizing a totally occluded femoral artery downstream of the profunda femoris.

As should be appreciated from the foregoing the subject invention provides a viable means for effecting the revascularization of partially or totally occluded coronary bypass grafts, while positively assuring that any debris particles produced during the revascularization procedure is removed from the patient's body. In addition, the subject invention is suitable for revascularizing other occluded vessels, as well. For example, in FIG. 5 the system is shown in use revascularizing a totally occluded femoral artery 18 downstream of the profunda femoris 18A. In this application the system functions to capture the debris created during the lumen opening procedure by preventing it from going along side the catheter and exiting down the profunda to end up in the distal capillary beds. In this application, a portion $Q_4+Q_1-Q_2$ of the blood flowing down the femoral artery 18 to the situs of the occlusion will be permitted to flow into the profunda femoris, while the portion $Q_2-Q_1$ of the blood and infusate liquid is diverted and/or withdrawn into the guide catheter to ensure positive debris removal in the same manner as described earlier. For some persons, e.g., diabetics with severely compromised distal capillary beds, a femoral artery revascularization procedure is likely to prove beneficial.

It must be reiterated that the atherectomy catheter for producing the lumen through the vascular occlusion need not be a rotary impacting device, like described above. Thus, a system 20 constructed in accordance with this invention may make use of any instrument having any type of working head, e.g., a reciprocating impacting working head, a combined rotary and reciprocating impacting working head, a rotary cutting head, a reciprocating cutting head, a rotary abrasive head, etc., to open the lumen in the occlusive material in the blood vessel. Moreover, the working head need not be shrouded. In fact, any of the heretofore identified prior art atherectomy devices can be utilized as part of the system 20. Some thrombectomy devices may also be utilized as part of the system 20. One such potential device is the Amplatz Thrombectomy Device designated by the trademark CLOT BUSTER by Microvena Corporation. It should also be pointed out that the working head of the device for forming the lumen need not even engage the occlusive material, so long as its lumen-opening operation produces debris particles to be removed. Thus, devices making use of liquid jets, laser beams, etc., can be utilized to open the lumen as part of the system of this invention. In short, any type of instrument for opening a lumen through the occlusive material and which produces debris can benefit from use in the system of this invention, i.e., a system which establishes a differential flow, wherein the infusate flow is less than the aspiration flow so that particles or pieces of occlusive material removed are positively precluded from flowing into adjacent vessels. Moreover, while the production of a local vortex flow adjacent the working head is desirable to effectuate the lumen opening process and to reduce debris particle size, it is not crucial to this invention.

Without further elaboration the foregoing will so fully illustrate our invention that others may, by applying current or future knowledge, adopt the same for use under various conditions of service.

What is claimed:

1. A system for removing occlusive material from an occluded blood vessel portion of a living being's vascular system, comprising:

an elongated flexible tubular body member having a free end adapted to be delivered intravascularly to the occluded blood vessel portion and deliver a jet of infusate liquid into said vessel to dislodge particles of said occlusive material;

an infusate pump for delivering said infusate liquid to said occluded blood vessel portion at an infusate flow rate; and an aspiration pump for aspirating infusate liquid, blood and dislodged particles from the occluded blood vessel portion at an aspiration flow rate;

wherein said aspiration flow rate is greater than said infusate flow rate and said infusate and aspiration pumps are simultaneously operable to create a differential flow rate in said occluded blood vessel portion and thereby prevent particles of occlusive material from flowing into any upstream blood vessel or downstream blood vessel in said living being's vascular system.

2. The system according to claim 1, further comprising a guide catheter.

3. The system according to claim 1, further comprising a collection vessel located outside the body of said living being.

4. The system according to claim 1, wherein the aspiration flow rate is in the range of 5 to 100 ml per minute.

5. The system according to claim 1, wherein the aspiration flow rate exceeds the infusion flow rate by between 5 and 50 percent.

6. The system according to claim 1, wherein said aspiration flow rate and said infusion flow rates are variable.

7. The system according to claim 1, wherein said infusate and aspiration pumps are piston pumps.

8. The system according to claim 1, wherein said infusate and aspiration pumps are peristaltic pumps.

9. The system according to claim 1, wherein said elongated flexible tubular body is adapted to direct said jet of liquid laterally toward the wall of said blood vessel.

10. The system according to claim 1, wherein said aspiration flow rate and said infusion flow rate are coordinated, so that a change in one flow rate automatically results in a proportional change in the other flow rate.

11. The system according to claim 1, further comprising an electrical controller for controlling said infusate flow rate and said aspiration flow rate.

12. The system according to claim 11, wherein said controller automatically coordinates said aspiration flow rate and said infusion flow rate, so that a change in one flow rate automatically results in a proportional change in the other flow rate.

13. A method for removing occlusive material from an occluded blood vessel portion of a living being's vascular system, comprising:
providing a system comprising:
(i) an elongated flexible tubular body member having a free end adapted to be delivered intravascularly to the occluded blood vessel portion and deliver a jet of infusate liquid into said vessel to dislodge particles of said occlusive material;
(ii) an infusate pump for delivering said infusate liquid, at an infusate flow rate; and
(iii) an aspiration pump for aspirating infusate liquid, blood and occlusive material from the occluded blood vessel portion at an aspiration flow rate;
simultaneously aspirating infusate liquid, blood and dislodged particles from the occluded blood vessel portion at an aspiration flow rate that is greater than said infusate flow rate to create a differential flow rate in said occluded blood vessel portion and thereby prevent particles of occlusive material from flowing into any upstream blood vessel or downstream blood vessel in said living being's vascular system.

14. The method according to claim 13, wherein the infusate liquid contains a therapeutic drug.

15. The method according to claim 13, wherein the infusate liquid contains a contrast medium.

16. The method according to claim 13, wherein the aspiration flow rate is in the range of 5 to 100 ml per minute.

17. The method according to claim 13, wherein the aspiration flow rate exceeds the infusion flow rate by between 5 and 50 percent.

18. The method according to claim 13, wherein said aspiration flow rate and said infusion flow rates are variable.

19. The method according to claim 13, wherein said aspiration flow rate and said infusion flow rate are coordinated, so that a change in one flow rate automatically results in a proportional change in the other flow rate.

20. The method according to claim 13, wherein said system further comprises an electrical controller for controlling said infusate flow rate and said aspiration flow rate.

21. The method according to claim 20, wherein said controller automatically coordinates said aspiration flow rate and said infusion flow rate, so that a change in one flow rate automatically results in a proportional change in the other flow rate.

22. The method according to claim 13, wherein said infusate and aspiration pumps are piston pumps.

23. The method according to claim 13, wherein said infusate and aspiration pumps are peristaltic pumps.

24. The method according to claim 13, wherein said elongated flexible tubular body is adapted to direct said jet of liquid laterally toward the wall of said blood vessel.

25. A system for removing occlusive material from a blood vessel portion of a living being's vascular system comprising:
an elongated flexible tubular body member adapted to be delivered intravascularly to the occluded portion of a blood vessel;
an infusate pump for delivery an infusate liquid at an infusate flow rate into said blood vessel; and
an aspiration pump for aspirating said infusate liquid and said occlusive material at an aspiration flow rate,
wherein said infusate flow rate is less than said aspiration flow rate, and wherein said rates serve to prevent embolization of said occlusive material in the living being's vascular system.

26. The system of claim 25 wherein said tubular body member is arranged to deliver said infusate liquid in the form of a liquid jet that serves to dislodge particles of said occlusive material to open the lumen.

27. The system of claim 26 wherein said tubular body member comprises a working head arranged to dislodge particles of said occlusive material.

28. The system of claim 27 wherein said working head is arranged to deliver said infusate liquid in the form of a jet.

29. The system of claim 25 wherein said infusate comprises at least one of a contrast medium, a drug, or an oxygenated fluid.

30. The system of claim 29, wherein the drug is heparin or urokinase.

31. The system of claim 25 wherein said tubular body member is arranged to act on the occlusive material to produce debris.

32. The system of claim 31 wherein said tubular body member comprises an atherectomy device or a thrombolectomy device.

33. The system of claim 25 wherein said infusate flow rate and said aspiration flow rate are coordinated, such that a change in one flow rate automatically causes a proportional change in the other flow rate.

34. The system of claim 33 further comprising a mechanical linkage between said infusate pump and said aspiration pump.

* * * * *